US012691154B2

(12) United States Patent
Hwang

(10) Patent No.: US 12,691,154 B2
(45) Date of Patent: Jul. 28, 2026

(54) METHOD FOR MANUFACTURING BONE GROWTH PROMOTING COMPOSITION

(71) Applicant: Man Ki Hwang, Seoul (KR)

(72) Inventor: Man Ki Hwang, Seoul (KR)

( * ) Notice: Subject to any disclaimer, the term of this patent is extended or adjusted under 35 U.S.C. 154(b) by 324 days.

(21) Appl. No.: 18/545,477

(22) Filed: Dec. 19, 2023

(65) Prior Publication Data

US 2024/0207346 A1 Jun. 27, 2024

(30) Foreign Application Priority Data

Dec. 21, 2022 (KR) ........................ 10-2022-0180592

(51) Int. Cl.
| | |
|---|---|
| *A61K 36/481* | (2006.01) |
| *A61K 36/03* | (2006.01) |
| *A61K 36/254* | (2006.01) |
| *A61K 36/45* | (2006.01) |
| *A61K 36/53* | (2006.01) |
| *A61K 36/9066* | (2006.01) |
| *A61P 19/00* | (2006.01) |

(52) U.S. Cl.
CPC ............ *A61K 36/481* (2013.01); *A61K 36/03* (2013.01); *A61K 36/254* (2013.01); *A61K 36/45* (2013.01); *A61K 36/53* (2013.01); *A61K 36/9066* (2013.01); *A61P 19/00* (2018.01)

(58) Field of Classification Search
CPC .... A61K 36/481; A61K 36/03; A61K 36/254; A61K 36/45; A61K 36/53; A61K 36/9066; A61P 19/00
See application file for complete search history.

(56) References Cited

FOREIGN PATENT DOCUMENTS

| | | | | |
|---|---|---|---|---|
| CN | 101011565 A | * | 8/2007 | |
| KR | 10-2016-0001392 A | | 1/2016 | |
| KR | 10-1626938 B1 | | 6/2016 | |
| WO | WO-2017185038 A1 | * | 10/2017 | ............. A61P 37/08 |

OTHER PUBLICATIONS

Leone-Bay Andrea, Fast-Acting Plant-Based Medicinal Compounds and Nutritional Supplements, Oct. 26, 2017, WO-2017185038-A1, 64pages, Year 2017; English translation.*
Gao, Shu-hua, A health food with oxidation resistance and the function of increasing bone density and health protection, Aug. 8, 2007, CN-101011565-A, 8pages, Year 2007; English translation.*
Kim Ji Young, Composition Comprising the Combined Extracts of Phlomis Umbrosa, Astragalus Membranceus, Discorea Japonica, Acanthpanax Senticosus and Angelica Gigas for Stimulating Bone Growth, Jun. 6, 2016, KR-20160001392-A, 9 pages, Year 2016; machine translation.*
Choong Ho Shin, M.D.,<"Current use of growth hormone in children">, Korean Journal of Pediatrics, Department of Pediatrics, College of Medicine, Seoul National University, Seoul, Korea, 2006, vol. 19, No. 7, pp. 703-709.
<Korean Decision on Registration Office Action for Korean Application No. 10-2022-0180592 dated Mar. 3, 2023, 9 pages>.
<Korean Office Action for Korean Application No. 10-2022-0180592 dated Jan. 27, 2023, 4 pages >.

* cited by examiner

*Primary Examiner* — Anand U Desai
*Assistant Examiner* — Alpa Nilesh Amin
(74) *Attorney, Agent, or Firm* — Sughrue Mion, PLLC

(57) ABSTRACT

Disclosed herein is a method for manufacturing a bone growth promoting composition including preparing a mixture by mixing *Astragalus membranceus, Acanthopanax senticosus, Phlomis umbrosa*, and bilberry, fermenting the mixture primarily, drying and grinding the mixture into a powder, extracting liquid from the powder, and fermenting the liquid secondarily.

1 Claim, No Drawings

METHOD FOR MANUFACTURING BONE GROWTH PROMOTING COMPOSITION

CROSS-REFERENCE TO RELATED APPLICATION

This application claims priority to and the benefit of Korean Patent Application No. 2022-0180592, filed on Dec. 21, 2022, the disclosure of which is incorporated herein by reference in its entirety.

BACKGROUND

1. Field of the Invention

The present disclosure relates to a method for manufacturing a bone growth promoting composition, and more particularly to a method for manufacturing a bone growth promoting composition that contains extracts containing *Astragalus membranceus, Acanthopanax senticosus, Phlomis umbrosa*, and bilberry as active ingredients, and is capable of promoting bone growth and preventing precocious puberty.

2. Description of the Related Art

Short stature is defined as height that is less than 3% (the third smallest out of 100) of the normal distribution of height for children of the same age of the same gender. There are two types of short stature: normal variant short stature, which does not involve a disease but is caused by a genetic predisposition and constitutional shortness, and short stature secondary to a disease.

Normal variant short stature can be categorized into familial short stature, constitutional growth retardation, or idiopathic short stature. Familial short stature is a case of genetic short stature, while constitutional growth retardation is a case of late constitutional growth, which is characterized by a short stature at the time of birth but delayed puberty, resulting in late growth until the final adult height reaches the normal range. In addition, idiopathic short stature generally refers to children whose height is less than −2 standard deviation points below the mean or below the 3rd percentile, with no cause for short stature and with normal birth weight, normal limb and trunkcus (spine) body shape, adequate nutrition, no psychosocial problems, and normal growth hormone secretion (Shin, Chung-Ho, Recent Advances in Growth Hormone Therapy, Korean J Ped. Vol. 49. No. 7. 2006).

Short stature secondary to disease is categorized into primary growth disorders (endogenous disorders) and secondary growth disorders (exogenous disorders). Primary growth disorders include osteochondral dysplasia, short stature due to chromosomal abnormalities (Down syndrome or Turner syndrome), unreasonably low birth weight (intra-uterine growth retardation), short stature due to Freder-Willie syndrome, short stature due to Russell-Silver syndrome, and short stature due to Noonan syndrome. Further, the secondary growth disorders may include short stature due to nutritional deficiencies, short stature due to chronic systemic diseases, short stature due to growth hormone deficiency, short stature due to hypothyroidism, short stature due to precocious puberty, short stature due to Cushing's syndrome, and psychosocial dwarfism.

PRIOR ART LITERATURE (Patent Document 1) Korean Patent No. 10-1626938 (May 27, 2016)

SUMMARY OF THE DISCLOSURE

Therefore, the present disclosure has been made in view of the above problems, and it is an object of the present disclosure to provide a method for manufacturing a bone growth promoting composition including preparing a mixture by mixing *Astragalus membranceus, Acanthopanax senticosus, Phlomis umbrosa*, and bilberry, fermenting the mixture primarily, drying and grinding the mixture into a powder, extracting liquid from the powder, and fermenting the liquid secondarily.

In accordance with the present disclosure, the above and other objects can be accomplished by the provision of a method for manufacturing a bone growth promoting composition, including preparing a mixture by mixing *Astragalus membranceus, Acanthopanax senticosus, Phlomis umbrosa*, and bilberry, fermenting the mixture primarily, drying and grinding the mixture into a powder, extracting a liquid from the powder, and fermenting the liquid secondarily.

According to one embodiment of the present disclosure, the composition 20-30 parts by weight of *Astragalus membranceus*, 10-20 parts by weight of *Acanthopanax senticosus*, 5-10 parts by weight of *Phlomis umbrosa* and 5-10 parts by weight of bilberry.

According to one embodiment of the present disclosure, the primary fermenting of the mixture according to one embodiment of the present disclosure includes fermenting the mixture in 1-5 parts by weight of kelp vinegar at a temperature of 45° C. for 1 hour.

According to one embodiment of the present disclosure, the extracting of the liquid from the powder includes adding carbon dioxide pressurized to 8 MPa at a temperature of 35° C. to the powder to extract the liquid.

According to one embodiment of the present disclosure, the secondary fermenting of the mixture includes adding 1-5 parts by weight of turmeric vinegar to the liquid and fermenting the liquid at 45° C. for 1 hour.

DETAILED DESCRIPTION OF THE DISCLOSURE

Hereinafter, specific details for practicing the present disclosure are described in detail. However, in the following description, detailed descriptions of widely known functions or configurations are omitted to avoid obscuring the main points of the present disclosure unnecessarily.

The terms used in this specification will be briefly described, and then embodiments of the present disclosure will be described in detail. Although the terms used in this specification are selected, as much as possible, from general terms that are widely used at present while taking into consideration the functions obtained in accordance with at least one embodiment, these terms may be replaced by other terms based on intentions of those skilled in the art, judicial precedent, emergence of new technologies, or the like. Additionally, in a particular case, terms that are arbitrarily selected by the applicant may be used. In this case, meanings of these terms will be disclosed in detail in the corresponding description of the present disclosure. Accordingly, the terms used herein should be defined based on practical meanings thereof and the whole content of this specification, rather than being simply construed based on names of the terms.

A singular expression includes a plural expression unless the context clearly dictates otherwise. In addition, plural expressions include singular expressions unless the context clearly indicates that they are plural.

Throughout this specification, when a part "includes" a component, it means that the part may further include other components, rather than excluding the other components, unless otherwise stated.

As used throughout this specification, the terms "approximately," "substantially," and the like are intended to be inclusive of tolerances when tolerances exist.

Throughout this specification, the term "combination(s) thereof" as used in a Makushi-style expression means a mixture or combination of one or more selected from a group of components described in the Makushi-style expression.

Throughout this specification, references to "A and/or B" shall mean "A, or B, or A and B".

Hereinafter, embodiments of the present disclosure will be described in detail so that those skilled in the art can easily practice the present disclosure. The present disclosure may, however, be embodied in many different forms and should not be construed as limited to the embodiments set forth herein.

A method for manufacturing a bone growth promoting composition according to one embodiment of the present disclosure includes preparing a mixture of *Astragalus membranceus, Acanthopanax senticosus, Phlomis umbrosa*, and bilberry, fermenting the mixture primarily, drying and grinding the mixture into a powder, extracting liquid from the powder, and fermenting the liquid secondarily.

The operation of preparing the mixture of *Astragalus membranceus, Acanthopanax senticosus, Phlomis umbrosa* and bilberry according to the present disclosure includes 20-30 parts by weight of *Astragalus membranceus*, 10-20 parts by weight of *Acanthopanax senticosus*, 5-10 parts by weight of *Phlomis umbrosa* and 5-10 parts by weight of bilberry.

The composition according to the present disclosure includes 20-30 parts by weight of *Astragalus membranceus*.

According to the present disclosure, *Astragalus membranceus*, which is the nearly peeled root of *Astragalus membranceus*, a perennial herbaceous plant belonging to the Leguminosae family, contains sucrose, glucoronic acid, various amino acids, bitter principle, mucilage, choline, betaine, and folic acid.

The major components of *Astragalus membranceus* according to the present disclosure include triterpenoids, isoflavonoids, and polysaccharides. The isoflavonoids contain formononetin and calycosin. The isoflavonoids are phytoestrogens, which are known to be a natural alternative to female sex hormones.

The leaves, shoots or roots of *Astragalus membranceus* according to the present disclosure can be used. Preferably, the roots may be used.

The composition according to the present disclosure includes 10-20 parts by weight of *Acanthopanax senticosus*.

*Acanthopanax senticosus* according to the present disclosure is the dried root, rhizome and bark of *Acanthopanax senticosus*, a deciduous shrub of the family Araliaceae, and has been reported to have sedative, anti-stress, immunostimulant, smooth muscle relaxant and anti-inflammatory effects, and to protect the spleen, add energy, nourish the kidneys, stabilize the mind, strengthen the waist, and circulate blood.

The leaves, stems, roots, or fruits of *Acanthopanax senticosus* according to the present disclosure may be used. Preferably, the stems are used.

*Astragalus membranceus* and *Acanthopanax senticosus* according to the present disclosure have the effect of promoting bone growth by increasing the production of receptors of the pituitary gland (GHRH and GHS), which promote the secretion of growth hormone (GH), and by increasing growth factor (IGF-1), which promotes growth.

The composition according to the present disclosure includes 5-10 parts by weight of *Phlomis umbrosa*.

*Phlomis umbrosa* according to the present disclosure is a perennial herb belonging to the family Labiatae, distinct from *Dipsacus asper* Wall of the family Dipsacucear, and is used to strengthen muscles and bones, communicate blood vessels, and support the liver and kidney functions, and is used for arthritis, premature ejaculation, anemia, and the like.

Young leaves and roots of the *Phlomis umbrosa* according to the present disclosure can be used. Preferably, the roots can be used.

The *Phlomis umbrosa* according to the present disclosure exhibits similarity to phytohormones, and thus serves to stabilize sex hormones that are rapidly increased due to their lower activity than body hormones.

The composition according to the present disclosure includes 5-10 parts by weight of bilberry.

The bilberry (*Vaccinium myrtillus*) according to the present disclosure, which is a perennial plant, contains vitamins C and E, and has excellent antioxidant effects as a source of fiber.

The composition according to the present disclosure contains *Astragalus membranceus, Acanthopanax senticosus, Phlomis umbrosa*, and bilberry as active ingredients and may contain at least one auxiliary ingredient, for example, 45-50 parts by weight of purified water, 30-35 parts by weight of cyclo-P, 15-20 parts by weight of isomaltooligosaccharide, 2.5-5 parts by weight of green grape concentrate, 1.7-2.0 parts by weight of grape flavored jelly, 0.8-1.5 parts by weight of citric acid, 0.5-1.0 parts by weight of white sugar, 0.15-0.20 parts by weight of Keltrol T Plus, 0.1-0.2 parts by weight of sucralose, 0.1-0.2 parts by weight of *Scutellaria baicalensis* complex extract liquid, 0.1-0.2 parts by weight of Dolichoris semen extract powder, 0.01-0.02 parts by weight of organic vegetable mixture powder, 0.01-0.02 parts by weight of ferric pyrophosphate (24-26%), 0.01-0.02 parts by weight of zinc gluconate, 0.01-0.02 parts by weight of magnesium oxide, 0.01-0.02 parts by weight of a combination of *Phyllostachys pubescens* and *Scutellaria baicalensis* extracts powder, and 0.01-0.02 parts by weight of deer antler ferment extract powder.

The bilberry according to the present disclosure may be incorporated into the mixture in the form of a juice. For example, the bilberry is frozen at −5° C. to −10° C., washed to remove leaves, impurities, and the like, and warmed to 10° C. to 20° C. The warmed bilberry is juiced by the NFC (Not From Concentrate) method, and the juice is pasteurized at 10° C. for 30 seconds to prepare a bilberry juice.

The method for manufacturing a bone growth promoting composition according to one embodiment of the present disclosure includes fermenting the mixture primarily.

The primary fermenting of the mixture according to one embodiment of the present disclosure includes fermenting the mixture in 1-5 parts by weight of kelp vinegar at a temperature of 45° C. for 1 hour.

The kelp according to the present disclosure contains alginate as a major component. The polymannuronate contained in alginate prevents precocious puberty by inhibiting the secretion of leptin, which stimulates the secretion of sex hormones.

Leptin is a protein secreted by fat cells that stimulates the release of sex hormones, resulting in precocious puberty, which accelerates the onset of secondary sexual characteristics.

The primary fermenting of the mixture according to the present disclosure uses kelp vinegar to break down the cellulose in the mixture containing *Astragalus membranceus, Acanthopanax senticosus*, and *Phlomis umbrosa* to facilitate extraction and to inhibit leptin, which causes precocious puberty.

The method for manufacturing a bone growth promoting composition according to one embodiment of the present disclosure includes drying the mixture and grinding the same into a powder.

The mixture according to the present disclosure is dried at 60° C. and ground into a powder with a particle size of 0.1-0.5 cm.

The method for manufacturing a bone growth promoting composition according to one embodiment of the present disclosure includes extracting a liquid from the powder.

The extracting of the liquid from the powder includes adding carbon dioxide pressurized to 8 MPa at a temperature of 35° C. to the powder to extract the liquid.

The extracting of the liquid from the powder according to the present disclosure uses carbon dioxide pressurized to 8 MPa at 35° C. as a solvent to efficiently extract the liquid at a lower temperature.

The extraction using carbon dioxide as a solvent provides the effect of obtaining the components contained in the powder in the highest possible yield without denaturation.

The method for manufacturing a bone growth promoting composition according to one embodiment of the present disclosure includes fermenting the liquid secondarily.

The secondary fermenting of the liquid according to one embodiment of the present disclosure includes adding 1-5 parts by weight of turmeric vinegar and fermenting the same at a temperature of 45° C. for 1 hour.

The turmeric according to the present disclosure contains curcumin as a major component. Curcumin inhibits squalene synthase, which is involved in the biosynthesis of cholesterol, and suppresses the production of PPARγ and C/EBPα, which are involved in the differentiation and dysfunction of adipocytes, thereby inhibiting the secretion of leptin, which promotes sex hormones, and preventing precocious puberty.

The secondary fermenting of the mixture according to the present disclosure provides an effect of inhibiting leptin by adding 1-5 parts by weight of turmeric vinegar to the liquid and fermenting the liquid at 45° C. for 1 hour.

The present invention will be described in more detail below with reference to embodiments of the present disclosure. However, it should be noted that these embodiments are intended to illustrate the present invention, and the present invention is not limited by these embodiments.

Embodiment 1

To manufacture the bone growth promoting composition according to the present disclosure, 25 parts by weight of *Astragalus membranceus*, 15 parts by weight of Acanthopanax senticosus, 5 parts by weight of *Phlomis umbrosa*, and 5 parts by weight of bilberry were mixed as active ingredients with 45 parts by weight of purified water, 30 parts by weight of cyclo-P, 15 parts by weight of isomalto-oligosaccharide, 2.5 parts by weight of green grape concentrate, 1.7 parts by weight of grape flavored jelly, 0.8 parts by weight of citric acid, 0.5 parts by weight of white sugar, 0.15 parts by weight of Keltrol T Plus, 0.1 parts by weight of sucralose, 0.1 parts by weight of *Scutellaria baicalensis* complex extract liquid, 0.1 parts by weight of Dolichoris semen extract powder, 0.01 parts by weight of organic vegetable mixture powder, 0.01 parts by weight of ferric pyrophosphate (24-26%), 0.01 parts by weight of zinc gluconate, 0.01 parts by weight of magnesium oxide, 0.01 parts by weight of a combination of *Phyllostachys pubescens* and *Scutellaria baicalensis* extracts powder, and 0.01 parts by weight of deer antler ferment extract powder added to the mixture. 5 parts by weight of bilberry obtained by freezing the bilberry at −10° C., and then cleaning bilberry by removing leaves, impurities, and the like, juicing the bilberry warmed to 15° C. by the NFC method and pasteurizing the juice at 10°C. for 30 seconds were added to the mixture, and 5 parts by weight of kelp vinegar were added to the mixture. Then, the mixture was fermented at a temperature of 45° C. for 1 hour. The fermented mixture was dried at a temperature of 60° C., and ground to a powder with a particle size of 0. 3 cm particle size powder, extracted into a liquid by adding carbon dioxide pressurized to 8 Mpa at a temperature of 35° C. to the powder. Then, 5 parts by weight of turmeric vinegar was added to the liquid and the liquid was fermented at a temperature of 45° C. for 1 hour to complete the bone growth promoting composition.

Comparative Example 1

A nutritional supplement based on astragalus complex extract (HT042), which is commercially available, was used.

Comparative Example 2

The bone growth promoting composition was manufactured in the same manner as in Embodiment 1, except that instead of adding 5 parts by weight of kelp vinegar to the mixture and fermenting the mixture at 45° C. for 1 hour, and adding 5 parts by weight of turmeric vinegar to the liquid and fermenting the liquid at 45° C. for 1 hour, the bone growth promoting composition was manufactured by drying the mixture immediately and grinding the mixture into a powder without adding 5 parts by weight of kelp vinegar to the mixture and fermenting the mixture at 45° C. for 1 hour.

Comparative Example 3

The bone growth promoting composition was manufactured in the same manner as in Embodiment 1, except that instead of adding 5 parts by weight of kelp vinegar to the mixture and fermenting the mixture at 45° C. for 1 hour, and adding 5 parts by weight of turmeric vinegar to the liquid and fermenting the liquid at 45° C. for 1 hour, the composition was manufactured directly from the liquid without adding 5 parts by weight of turmeric vinegar to the liquid and fermenting the liquid at 45° C. for 1 hour.

Comparative Example 4

The bone growth promoting composition was manufactured in the same manner as in Embodiment 1, except that instead of adding 5 parts by weight of kelp vinegar to the mixture and fermenting the mixture at 45° C. for 1 hour, and adding 5 parts by weight of turmeric vinegar to the liquid and fermenting the liquid at 45° C. for 1 hour, the bone growth promoting composition was manufactured by adding 0.1 parts by weight of kelp vinegar to the mixture and fermenting the mixture at 45° C. for 1 hour.

Comparative Example 5

The bone growth promoting composition was manufactured in the same manner as in Embodiment 1, except that instead of adding 5 parts by weight of kelp vinegar to the mixture and fermenting the mixture at 45° C. for 1 hour, and adding 5 parts by weight of turmeric vinegar to the liquid and fermenting the liquid at 45° C. for 1 hour, the bone growth promoting composition was manufactured by adding 20 parts by weight of kelp vinegar to the mixture and fermenting the mixture at 45° C. for 1 hour.

Comparative Example 6

The bone growth promoting composition was manufactured in the same manner as in Embodiment 1, except that instead of adding 5 parts by weight of kelp vinegar to the mixture and fermenting the mixture at 45°C. for 1 hour, and adding 5 parts by weight of turmeric vinegar to the liquid and fermenting the liquid at 45° C. for 1 hour, the composition was manufactured by adding 0.1 parts by weight of turmeric vinegar to the liquid and fermenting the liquid at 45° C. for 1 hour.

Comparative Example 7

The bone growth promoting composition was manufactured in the same manner as in Embodiment 1, except that instead of adding 5 parts by weight of kelp vinegar to the mixture and fermenting the mixture at 45° C. for 1 hour, and adding 5 parts by weight of turmeric vinegar to the liquid and fermenting the liquid at 45° C. for 1 hour, the composition was manufactured by adding 20 parts by weight of turmeric vinegar to the liquid and fermenting the liquid at 45° C. for 1 hour.

Experimental Example 1: Bone Growth Test

Bone growth and density change measurements for the bone growth promoting composition were performed for Embodiment 1 and Comparative examples 1 to 7, respectively.

Bone length and density were measured to confirm bone growth for the bone growth promoting compositions for Embodiment 1 and Comparative examples 1 to 7. Twenty female juvenile albino rats with an average body weight of 130 g were prepared and tested for changes in bone growth and density upon consumption of each composition for one week. The level of addition of the composition was based on a 6th grade female student (36 kg body weight, 3 times daily, 100 ml per dose, total dose 300 ml, 0.83% of the body weight). The results are shown in Table 1 below.

TABLE 1

Results of Bone Length and Density Measurements

| | Bone length(cm) | Bone density(g/cm$^2$) |
| --- | --- | --- |
| Embodiment 1 | +0.87 | +0.0053 |
| Comparative example 1 | +0.31 | +0.0025 |

TABLE 1-continued

Results of Bone Length and Density Measurements

| | Bone length(cm) | Bone density(g/cm$^2$) |
| --- | --- | --- |
| Comparative example 2 | +0.42 | +0.0041 |
| Comparative example 3 | +0.41 | +0.0039 |
| Comparative example 4 | +0.45 | +0.0043 |
| Comparative example 5 | +0.47 | +0.0042 |
| Comparative example 6 | +0.44 | +0.0044 |
| Comparative example 7 | +0.46 | +0.0043 |

Based on the results in Table 1 above, it can be seen that the bone growth promoting composition of Embodiment 1 provides higher increases in bone growth and density than the products of Comparative examples 1 to 7.

More specifically, in the case of Embodiment 1, bone growth and density were found to be higher than in Comparative examples 1 and 7 by adding 5 parts by weight of kelp vinegar to the mixture, primarily fermenting the mixture for 1 hour at 45° C., adding 5 parts by weight of turmeric vinegar to the liquid and fermenting liquid secondarily for 1 hour at 45° C. It was confirmed that the primary fermentation by adding kelp vinegar to the mixture and the secondary fermentation by adding turmeric vinegar to the liquid were effective in increasing bone growth and density because the ingredients in the composition were uniformly decomposed and absorbed well when consumed, and the yield was high.

Experimental Example 2: Obesity Test

To determine the obesity level for the bone growth promoting composition for Embodiment 1 and Comparative examples 1 to 7, changes in total body weight, weight of the uterus and weight of the ovary were measured, and 20 female juvenile albino rats with an average body weight of 130 g were used to test the changes in body weight, weight of the uterus and weight of the ovary when the composition was consumed for 1 week. The level of addition of the composition was based on a 6th grade female student (36 kg body weight, 3 times daily, 100 ml per dose, total dose 300 ml, 0.83% of the body weight). The results are shown in Table 2 below.

TABLE 2

Results of Measuring Weight Change

| | Weight (g) | Uterus (g) | Ovary (g) |
| --- | --- | --- | --- |
| Embodiment 1 | +0.35 | +0.02 | +0.01 |
| Comparative example 1 | +0.70 | +0.09 | +0.05 |
| Comparative example 2 | +0.57 | +0.07 | +0.06 |
| Comparative example 3 | +0.58 | +0.06 | +0.06 |
| Comparative example 4 | +0.51 | +0.04 | +0.03 |
| Comparative example 5 | +0.49 | +0.05 | +0.03 |
| Comparative example 6 | +0.50 | +0.04 | +0.04 |
| Comparative example 7 | +0.51 | +0.05 | +0.03 |

Based on the results in Table 2 above, it can be seen that the bone growth promoting composition of Embodiment 1 provides lower increases in body weight than the products of Comparative examples 1 to 7.

More specifically, in the case of Embodiment 1, increase in weight was found to be lower than in Comparative examples 1 and 7 by adding 5 parts by weight of kelp vinegar to the mixture, primarily fermenting the mixture for 1 hour at 45° C., adding 5 parts by weight of turmeric vinegar to the liquid and fermenting liquid secondarily for 1 hour at 45° C. It was confirmed that the primary fermentation by adding kelp vinegar to the mixture and the secondary fermentation by adding turmeric vinegar to the liquid were effective in preventing obesity because it regulates leptin secreted by fat cells.

Experimental Example 3: Precocious Puberty Test

To determine the effect of the bone growth promoting composition on the precocious puberty for Embodiment 1 and Comparative examples 1 to 7, sex hormone concentrations in the blood were measured, and female juvenile albino rats with an average body weight of 130 g were used to test the change in the concentration of sex hormones (luteinizing hormone (LH), estrogen, follicle-stimulating hormone (FSH)) in the blood when the composition was consumed for one week. The level of addition of the composition was based on a 6th grade female student (36 kg body weight, 3 times daily, 100 ml per dose, total dose 300 ml, 0.83% of the body weight). The results are shown in Table 3 below.

TABLE 3

| Blood Sex Hormone Measurement Results | | | |
| --- | --- | --- | --- |
| | LH (ng/ml) | Estrogen (pg/ml) | FSH (ng/ml) |
| Embodiment 1 | +1.280 | +1.045 | +0.027 |
| Comparative example 1 | +2.301 | +2.089 | +0.065 |
| Comparative example 2 | +1.501 | +1.682 | +0.047 |
| Comparative example 3 | +1.634 | +1.527 | +0.048 |
| Comparative example 4 | +1.405 | +1.454 | +0.037 |
| Comparative example 5 | +1.398 | +1.435 | +0.034 |
| Comparative example 6 | +1.442 | +1.428 | +0.035 |
| Comparative example 7 | +1.403 | +1.498 | +0.036 |

Based on the results in Table 3 above, it can be seen that the bone growth promoting composition of Embodiment 1 provides more efficient regulation of sex hormone concentrations in the blood than the products of Comparative examples 1 to 7.

More specifically, in the case of Embodiment 1, increase in weight was found to be lower than in Comparative examples 1 and 7 by adding 5 parts by weight of kelp vinegar to the mixture, primarily fermenting the mixture for 1 hour at 45° C., adding 5 parts by weight of turmeric vinegar to the liquid and fermenting liquid secondarily for 1 hour at 45° C. It was confirmed that the primary fermentation by adding kelp vinegar to the mixture and the secondary fermentation by adding turmeric vinegar to the liquid were effective in preventing precocious puberty because it regulates leptin, which promotes sex hormones.

Compared to conventional methods for manufacturing a bone growth promoting composition, the method of manufacturing a bone growth promoting composition according to one embodiment of the present disclosure may provide a bone growth promoting composition that effectively promotes bone growth, prevents obesity and precocious puberty, and enhances the absorption of key ingredients.

As is apparent from the above description, the present disclosure provides the following effects.

A method for manufacturing a bone growth promoting composition according to the present disclosure may provide a composition capable of promoting bone growth.

The method for manufacturing a bone growth promoting composition according to the present disclosure may provide a composition capable of preventing precocious puberty.

The method for manufacturing a bone growth promoting composition according to the present disclosure may provide a composition that is easily digestible.

The method for manufacturing a bone growth promoting composition according to the present disclosure may provide a composition capable of promoting growth hormone.

The method for manufacturing a bone growth promoting composition according to the present disclosure may provide a composition capable of regulating sex hormones. The effects of the present disclosure are not limited to those mentioned above, and other effects not mentioned will be apparent to those skilled in the art from the claims.

The foregoing description of the disclosure is provided to enable those skilled in the art to practice or use the disclosure. Various modifications of the disclosure will be readily apparent to those skilled in the art, and the general principles defined herein may be applied to various modifications without departing from the spirit or scope of the disclosure. Accordingly, the disclosure is not intended to be limited to the examples described herein, but is intended to be given the broadest possible scope consistent with the principles and novel features disclosed herein.

While the present disclosure has been described in relation to some embodiments, it should be appreciated that various modifications and changes can be made without departing from the scope of the present disclosure as would be understood by one of ordinary skill in the art to which the present disclosure pertains. Further, such modifications and changes are to be considered as falling within the scope of the claims appended hereto.

What is claimed is:

1. A method for manufacturing a bone growth promoting composition, the method comprising:

preparing a mixture by mixing 25 parts by weight of *Astragalus membranceus*, 15 parts by weight of *Acanthopanax senticosus*, 5 parts by weight of *Phlomis umbrosa*, and 5 parts by weight of bilberry;

adding 5 parts by weight of kelp vinegar to the mixture and fermenting the mixture at a temperature of 45° C. for 1 hour;

drying the ferment fermented mixture and grinding the same into a powder;

extracting a liquid from the powder by adding carbon dioxide pressurized to 8 MPa at a temperature of 35° C. to the powder; and adding 5 parts by weight of turmeric vinegar to the liquid and fermenting the liquid at a temperature of 45° C. for 1 hour; and separating the fermented liquid to there by manufacture a bone growth composition comprising the fermented liquid.

\* \* \* \* \*